United States Patent [19]

Nordal et al.

[11] 4,250,113
[45] Feb. 10, 1981

[54] CHEMICAL COMPOUNDS

[75] Inventors: Vegard Nordal; Hugo Holtermann, both of Oslo, Norway

[73] Assignee: Nyegaard & Co. A/S, Oslo, Norway

[21] Appl. No.: 69,589

[22] Filed: Aug. 24, 1979

Related U.S. Application Data

[63] Continuation of Ser. No. 805,351, Jun. 10, 1977, abandoned.

[30] Foreign Application Priority Data

Jun. 11, 1976 [GB] United Kingdom ............ 24338/76

[51] Int. Cl.³ ........................................... C07C 103/26
[52] U.S. Cl. .................................. 564/153; 424/5
[58] Field of Search .............. 260/559 R, 558 A, 490, 260/211 A, 559 A; 424/5

[56] References Cited

U.S. PATENT DOCUMENTS 3,701,771  10/1972  Almen et al. ........................ 424/5
4,021,481   5/1977  Almen et al. ................... 260/558 A

FOREIGN PATENT DOCUMENTS 1321591  6/1973  United Kingdom .

Primary Examiner—Jacqueline V. Howard
Attorney, Agent, or Firm—Bacon & Thomas

[57] ABSTRACT

Compounds of the formula:

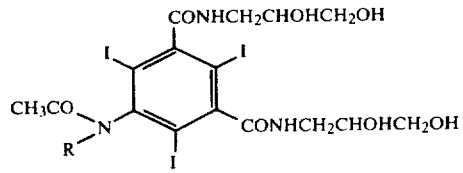

wherein R represents the group —$CH_2CH_2OH$ or —$CH_2CHOHCH_2OH$, particularly in racemic or optically active form, are employed as active ingredients in X-ray contrast agents for intracerebral, but particularly for vascular use. The compounds are prepared by reacting 5-(N-acetamido)-2,4,6-triiodo-N,N'-bis-(2,3-dihydroxypropyl)isophthalamide or an O-acetyl derivative thereof with an appropriate hydroxyalkylating agent and subsequently, if necessary, hydrolyzing any unwanted O-acetyl groups.

4 Claims, No Drawings

CHEMICAL COMPOUNDS

This is a continuation of application Ser. No. 805,351, filed June 10, 1977, now abandoned.

This invention relates to novel non-ionic iodinated X-ray contrast agents for intracerebral, but particularly for vascular use.

In our British patent specification No. 1,321,591 we describe and claim certain non-ionic iodinated compounds as X-ray contrast agents, such compounds representing an important advance over previously known ionic X-ray contrast agents in respect of side-effects due to high concentrations of ions or to high osmolality. Such compounds are suitable for one or more possible fields of X-ray visualisation but are not usually suitable for a wide range or spectrum of such uses. In general, non-ionic X-ray contrast agents may be of use in two main fields, namely:

Intravascular visualisation, including urography and angiography, for example cerebral, coronary and peripheral angiography, and Myelography, i.e. injection into the cerebrospinal fluid.

Hitherto, radiologists have used different X-ray contrast agents particularly adapted to different fields of use but there are clearly advantages if it is possible to use a single X-ray contrast agent for a wide range of uses; apart from economies of scale in manufacture, it is also more satisfactory for the radiologist to be able to use experience of a contrast agent gained in one field of use, e.g. urography, in some other field, e.g. angiography or myelography. For the purposes of this specification an X-ray contrast agent which can be used in all forms of intravascular visualisation and myelography is termed a 'general X-ray contrast agent'. A really useful general X-ray contrast agent should, however, possess a 'package' of favourable essential parameters, namely, low toxicity, low osmolality, low viscosity and high stability and the ability to produce solutions of high concentration but low ion concentration; it is very difficult to find compounds which are sufficiently straightforward to synthesise, and thus commercially practicable from the point of view of cost, and which possess every one of the above parameters to a satisfactory level. While the minimum standard for each parameter is not necessarily exceptionally high in itself, it is very unusual to find a compound which possesses, the whole 'package' of favourable properties at a suitably high level and can thus be used as a general X-ray contrast agent.

The above parameters are now considered in detail:

Toxicity

In the X-ray visualisation of relatively extensive regions of the human body, for example the vascular system or the cavities containing the cerebrospinal fluid, large quantities of X-ray contrast agents have to be injected in order to provide sufficient opacity in the region concerned. Consequently, the toxicity of the contrast agent at high concentration and/or at high dose levels is of great importance. In the visualisation of the vascular system a large number of compounds have been proposed as contrast agents and while many have been used successfully, their toxicity, although often very slight, does give rise to some undesirable side effects. In the visualisation of the cavities containing the cerebrospinal fluid, the highly concentrated compounds used in vascular visualisation are often far too toxic, although such visualisation is substantially less frequently used than vascular visualisation.

On the above basis, we have concluded that it is preferable that a compound should have an $LD_{50}$ i.v. in the mouse greater than or equal to 17,000 mg I/kg in order to fulfil the requirements of a particularly effective general X-ray contrast agent. In addition to intravenous toxicity it is necessary to consider nephrotoxicity which is of particular importance in relation to X-ray contrast agents for vascular use. In general, it is preferable that an X-ray contrast agent should not show any significant increase in clinicochemical parameters such as urea and creatinine levels at a dose level lower than 8000 mg I/kg (as determined in the rabbit). Furthermore, the intracerebral $LD_{50}$ of a general X-ray contrast agent is preferably at least 1500 mg I/kg in mice.

In order to gain water solubility, compounds have in the past been selected which carry an acidic group, for example a carboxylic acid or sulphuric acid group since their alkali metal salts and certain amine salts are frequently extremely water soluble and while several commercially used contrast agents of this type exhibit relatively low levels of toxicity intravenously, their use at high concentrations has been found to lead to undesirable side effects especially when they are injected into the cerebrospinal fluid.

In the vascular field N-methyl glucamine salts have been shown to cause heart fibrillation whereas sodium salts—at very high doses, cause lung oedema. These effects are believed to be caused by the cations per se.

In the subarachnoid space solutions containing N-methylglucammonium ions may cause a depressive effect resulting in respiratory failure and described blood pressure. Sodium ions have an opposite effect causing an increase in blood pressure and heart fibrillation.

Osmolality

In addition to toxic effects due to the cations, it is the considered opinion among specialists in radiology that these side effects are due, in part, to the osmotic imbalance created by injecting very large concentrations of dissolved material into the body fluids.

The osmolality of a solution of a chemical compound is normally approximately directly proportional to the sum of the concentrations of the different molecular or ionic species which are present. A water-soluble salt, for example the sodium salt of an iodinated acid, will normally be almost completely ionised and the osmolality will be proportional to the concentration of both the anion and the cation. The total concentration of ionic species will thus be approximately twice that of the salt considered as a single unionised species. In contrast, the osmolality of a non-ionic compound e.g. of the type described in our above British Patent Specification, that is a compound which is substantially unionised in aqueous solution, is expected to be approximately proportional simply to the molarity of the compound present, that is approximately half the value for an analogous ionic compound having two ionic species. An osmolality of about 0.75 Os/kg at 300 mg I/ml is preferable if a compound is to fulfil the requirements of a particularly preferred compound for use as a general X-ray contrast agent.

High concentrations

Aqueous solutions containing more than 270 mg I/ml are considered preferable for a compound to fulfil the requirements of a particularly preferred compound for use as a general X-ray contrast agent.

Viscosity

X-ray contrast agent for intracerebral and intravascular use are, in general, administered by injection. It is therefore important that the X-ray contrast agent employed should possess a viscosity sufficiently low to permit administration at acceptable rates of injection and to ensure physiological compatibility.

A viscosity of 6.5 cP or less at 37° C. (concentration 300 mg I/ml) is necessary if a compound is to fulfil the requirements of a particularly preferred compound for use as an X-ray contrast agent.

Stability

It is also important that X-ray contrast agents are chemically stable. Many compounds previously proposed for use as X-ray contrast agents have been found to undergo chemical changes when autoclaved and are clearly unsuitable. It is therefore considered necessary that a compound should be stable to autoclaving at 120° C. for 20 minutes if it is to fulfil the requirements of a particularly preferred compound for use as a general X-ray contrast agent.

Manufacture

Finally, a commercially viable general X-ray contrast agent must be simple enough (and therefore cheap enough) in manufacture to sell at an acceptable price. X-ray contrast agents are, in general, used in large quantities as compared with many compounds used in medicine and it is very important to keep their cost as low as possible.

The present invention is based upon the discovery that the following compounds:

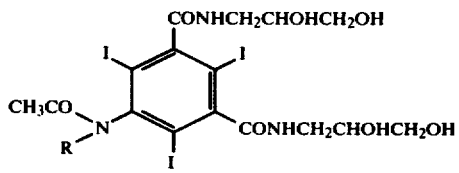

(wherein R represent the group —CH$_2$CH$_2$OH or —CH$_2$CHOHCH$_2$OH) which are not specifically disclosed in our British patent specification No. 1,321,591, possess, to at least the preferred levels indicated above, each of the properties of low toxicity, low osmolality, low viscosity, high stability and the ability to form solutions of high concentration and thus represent a substantial and valuable advance over the compounds generally disclosed in our above British Patent Specification.

The present invention thus relates to 5-(N-2-hydroxyethylacetamido-2,4,6-triiodo-N,N'-bis(2,3-dihydroxypropyl)isophthalamide (hereinafter called compound I) and to 5-(N-2,3-dihydroxypropylacetamido)-2,4,6-triiodo-N,N'-bis(2,3-dihydroxypropyl)isophthalamide (hereinafter called compound II). Compound I and compound II contain at least two chiral centres and thus exist in optically active form as described hereinafter in more detail. The present invention thus includes the d-, l-, racemic and meso-forms of compounds I and II.

The compound of formula I in which R represents the —CH$_2$CH$_2$OH group (Compound I) has been found to posses (1) an intravenous toxicity (LD$_{50}$ i.v.) in the mouse of 21,900 mg I/kg and an intracerebral toxicity (LD$_{50}$ i.c.) in the mouse of greater than 1500 mg I/kg; (2) nephrotoxicity in the rabbit greater than 10,500 mg I/kg; (3) the ability to form solutions of high concentration, i.e. at least 400–500 mg I/ml; (4) low osmolality: 0.46 Os/kg at a concentration of 280 mg I/ml, 0.64 Os/kg at a concentration of 380 mg I/ml, 0.50 at a concentration of 300 mg I/ml (determined by interpolation) and 0.50 (cryoscopic) at a concentration of 300 mg I/ml; and (5) a viscosity of 4.1 cP at 37° C. and 7.4 cP at 20° C., the concentration in each case being 280 mg I/ml; and a viscosity of 5.0 cP at 37° C. and 9.3 at 20° C., the concentration being 300 mg I/ml in each case.

The compound of formula I in which R represents the —CH$_2$CHOHCH$_2$OH group (Compound II) has been found to possess (1) an intravenous toxicity (LD$_{50}$ i.v.) in the mouse of 23,400 mg I/kg and an intracerebral toxicity (LD$_{50}$ i.c.) in the mouse of greater than 1500 mg I/kg; (2) nephrotoxicity in the rabbit greater than 10,500 mg I/kg; (3) the ability to form solutions of high concentration, i.e. at least 400–500 mg I/ml; (3) low viscosity of 6.2 cP at 37° C. and 12.6 cP at 20° C., the concentration in each case being 300 mg I/ml; and (4) low osmolality (cryoscopic) 0.65 Os/kg at a concentration of 300 mg I/ml.

With regard to stability both the compounds of formula I may be autoclaved at pH 5.

Thus the compounds of the present invention fulfil all the various criteria set out above regarding the properties of compounds of particular interest as X-ray contrast agents including ease of manufacture (see below).

The present invention also provides radiological compositions comprising as active ingredient a compound of formula I as hereinbefore defined in association with a radiological carrier.

The radiological compositions of the present invention are conveniently presented in a form suitable for administration by injection, for example, in ampoules or vials. The capacity of the ampoule or vial may be, for example, from 5 to 300 ml and the concentration may, for example, be from 20 to 500 mg I/ml.

The compounds of the present invention may be prepared in any convenient manner, but the following process is of particular interest and constitutes a further feature of the present invention.

Thus there is provided a process for the preparation of compounds of formula I as hereinbefore defined which comprises reacting a compound of the formula:

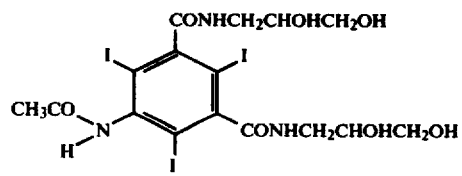

or an O- acetyl derivative thereof, with an appropriate hydroxyalkylating agent, for example, a compound of the formula:

R—X    III (wherein R is as hereinbefore defined and X represents an atom or group removable an anion) followed, where necessary, by hydrolysis of any unwanted O-acetyl groups whereby a compound of formula I as hereinbefore defined is obtained.

It will be appreciated that the hydroxyalkylating agent is selected to introduce either a 2-hydroxyethyl group or a 2,3-dihydroxypropyl group into the compound of formula II. Thus, for example, the compound of formula III preferably used is a reactive ester derivative such as a compound of formula III in which X represents a halogen atom e.g. a chlorine or bromine atom, or a sulphate or hydrocarbon-sulphate group e.g. a tosyl or mesyl group. The reactive derivative is preferably reacted with the acylamido starting material under basic conditions, for example in a non-aqueous medium, e.g. in an alkanol such as methanol or ethanol, the base conveniently being an alkali metal alkoxide such as sodium methoxide, or in an aqueous alkaline medium, for example containing an alkali metal hydroxide such as sodium or potassium hydroxide. It is also possible to react the acylamido compound with an epoxide, i.e. ethylene oxide or glycide.

Thus, for example, the compound of formula I in which R represents a 2-hydroxyethyl group may be prepared by reaction of the compound of formula II with 2-chloroethanol preferably in the presence of propylene glycol with, for example, sodium methoxide as base.

Similarly the compound of formula I in which R represents a 2,3-dihydroxypropyl group may, for example, be prepared by reaction of a compound of formula II with 3-chloropropan-1,2-diol preferably in the presence of propylene glycol with, for example, sodium methoxide as base.

The compound of formula II may be prepared in any convenient manner, for example, by reaction of 5-acetamido-2,4,6-triiodoisophthaloyl chloride and/or 5-diacetylamino-2,4,6-triiodoisophthaloyl chloride with 2,3-dihydroxypropylamine followed, where 5-diacetyl is used by removal of one N acetyl group, e.g. by alkaline hydrolysis at slightly elevated temperature. The reaction may, for example, be effected in the presence of dimethylformamide or dioxan as solvent, conveniently in the additional presence of an alkali metal or alkaline earth metal carbonate or bicarbonate such as potassium bicarbonate.

The compound of formula II may also be prepared, for example, by acetylation of a compound of the formula:

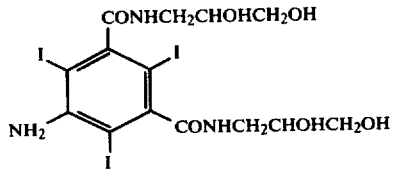

IV

Acetylation may be effected by any convenient method e.g. by the use of acetic anhydride (which can also serve as the solvent) together with catalytic amounts of a mineral acid e.g. sulphuric or perchloric acid, or by the use of an acid halide preferably in a polar solvent such as dimethylformamide or dimethylacetamide. Where unwanted O-acetyl groupings are formed these may be removed either at this stage or after the hydroxyalkylation of the O-acetylated compound. The basic hydrolysis of the O-acetyl grouping may for example, be effected using aqueous alkali metal hydroxide e.g. sodium hydroxide, the reaction preferably being carried out at slightly elevated temperature, e.g. about 50° C.

In addition, depending on the acylating agent used, other products may be formed and require separation. When an acyl anhydride such as acetic anhydride is used with concentrated sulphuric acid as catalyst, the primary amino group is often, in part, bis-acetylated, such that an overacetylated product is obtained. In general a mixture of acetylated products will be obtained. If desired, the bis-acetylamino group may be hydrolysed to the mono-acetylamino group under mild basic conditions e.g. by the use of sodium hydroxide in, for example, methanol prior to N-hydroxyalkylation. It is, however, possible to effect N-hydroxyalkylations using the bis-acetylamino compound with simultaneous solvolysis.

The compound of formula IV is preferably first prepared by iodination of 5-amino-N,N'-bis(2,3-dihydroxypropyl)isophthalamide. Iodination may, for example, be effected by the use of NaICl$_2$ or any other convenient iodinating agent.

The 5-amino-N,N'-bis(2,3-dihydroxypropyl)isophthalamide is preferably prepared by reduction of 5-nitro-N,N'-bis(2,3-dihydroxypropyl)isophthalamide, for example, by hydrogenation in the presence of a hydrogenation catalyst such as platinum, palladium or PdO/charcoal.

The 5-nitro-N,N'-bis(2,3-dihydroxypropyl)isophthalamide is preferably prepared by reaction of dimethyl 5-nitro-isophthalate with 3-amino-1,2-propanediol. The reaction may, for example, be effected at an elevated temperature e.g. in boiling methanol.

Thus in one embodiment of the present invention there is provided a convenient multi-stage process capable of producing the compounds of the present invention in high yield. It will be appreciated that a further advantage of the compounds of the present invention resides in the ease and high yield of their production compared with many previously disclosed compounds.

Thus, for example, there are two types of ionic 2,4,6-triodobenzoic acids used commercially at the present time, namely those derived from 3,5-diamino-2,4,6-triodobenzoic acid and those derived from 3-amino 2,4,6-triodoisophthalic acid. Most of the non-ionic X-ray contrast agents described in our above Patent specification are amide derivatives of these two classes. The only compound of the former type which possesses a package of parameters approaching the preferred minimum set out above is N-(N-methyl-3,5-diacetamido-2,4,6-triodobenzoyl)-D-glucamine although its intravascular toxicity, nephrotoxicity and viscosity are rather high. It will be seen that in this case the 3- and 5- amino groups are differently substituted; this compound is produced from 3,5-dinitrobenzoic acid by the following steps: (1) selective reduction of one nitro group; (2) acetylation of the amino group so formed; (3) reduction of the second nitro group; (4) triiodination; (5) methylation of the acetamido group; (6) conversion of the carboxyl group to acid halide; (7) acetylation of the free amino group; and (8) reaction with 1-glucamine (which is not commercially available and must additionally by synthesised). The methylation reaction (5) must be effected after the iodination reaction (4) if a completely selective reaction is to be achieved and since iodination is expensive, losses due to further reactions after iodination greatly increase the cost of the product.

Similarly, the only compound of the isophthalic acid type which possesses a package of parameters approaching the preferred minimum set out above is (3-acetamido-5-N-methylcarbamoyl-2,4,6-triodobenzoyl)-N-methylglucamine, although its solubility in water is unsatisfactory. This compound contains differently substituted carboxyl groups; it is prepared from 3-nitro-isophthalic acid by (1) selective mono-esterification; (2) amidation of the ester group with methylamine; (3) reduction of the nitro group; (4) iodination; (5) acetylation of the amino group; (6) conversion of the carboxyl group to acid halide; (7) reaction with N-methyl-glucamine. Again, it is necessary to carry out selective reactions and the second carbamoyl group must be introduced after the expensive triiodination step to ensure a selective reaction.

Both the above prior art compounds are described in our above Patent specification.

In contrast, the two compounds of the present invention, although they are derived from 3-nitro isophthalic acid, possess identical carbamoyl groupings and can be obtained by a 6-stage synthesis in which there are no selective reactions. The first stage is formation of a diester of the above acid and the remaining five stages are set out below.

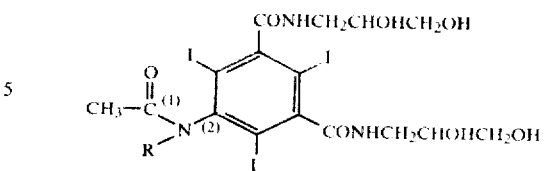

it will be appreciated that exo- and endo- isomers exist due to restricted rotation of the N-CO bond (1) caused by steric hindrance from the adjacent bulky iodine atoms and the presence of the hydroxyalkyl group R bonded to the said N-atom. These isomers tend to equil-

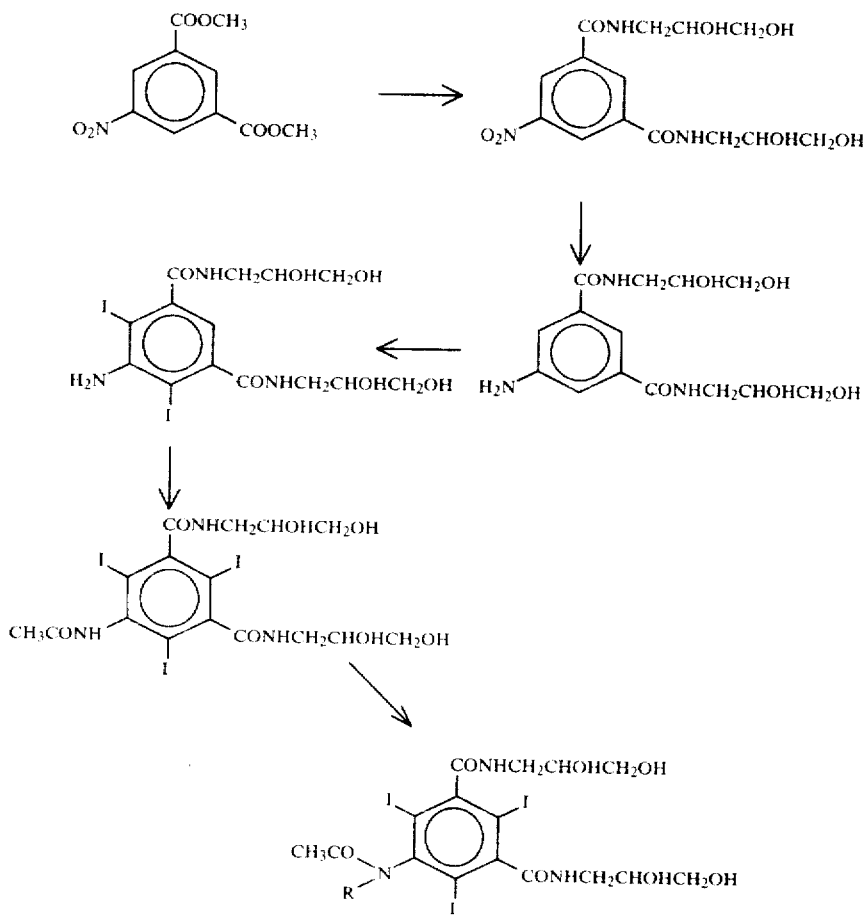

It will be seen that this process enables the compounds of the present invention to be conveniently prepared from readily available starting materials in high yield as compared with the above prior art compounds.

The compounds of the present invention are subject to a number of different types of isomerism as is explained below. The present invention extends to all of these isomeric forms. Referring to the following formula ibrate in solution but are sufficiently stable to be separated by thin layer chromatography.

The compounds of the present invention also exist in racemic, optically active and meso forms. There are two meso forms due to restricted rotation of the bond (2). Thus the compound of formula I in which R represents a 2-hydroxyethyl group exists as one racemic pair (Ia and Ib) and in two meso forms (Ic and Id) as illustrated below:

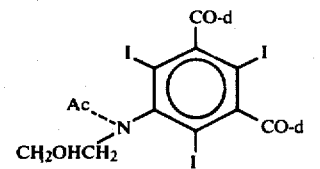

Ia

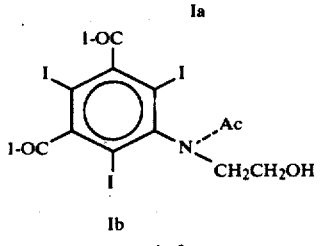

Ib
racemic form

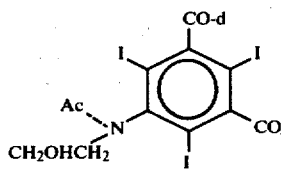

Ic

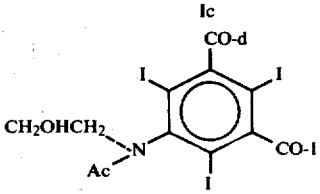

Id
meso forms
d-H: (+)-CH₂OHCHOHCH₂NH₂
l-H: (−)-CH₂OHCHOHCH₂NH₂

The compound of formula I in which R represents a 2,3-dihydroxypropyl group has one more asymmetric centre than the compound of formula I in which R represents a 2-hydroxyethyl group and thus exists in four racemic pairs as illustrated below:

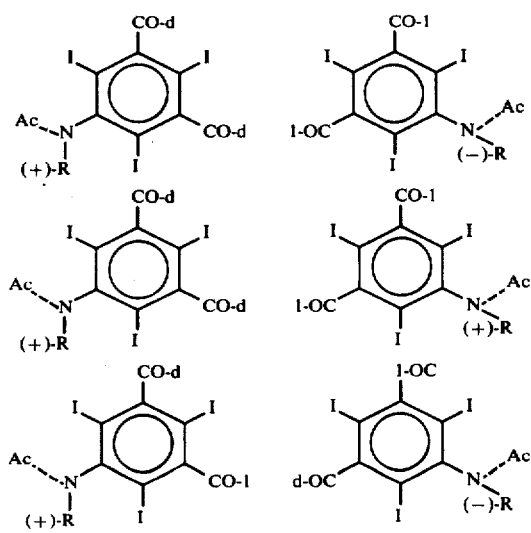

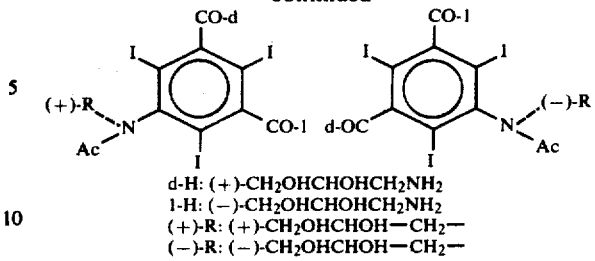

d-H: (+)-CH₂OHCHOHCH₂NH₂
l-H: (−)-CH₂OHCHOHCH₂NH₂
(+)-R: (+)-CH₂OHCHOH—CH₂—
(−)-R: (−)-CH₂OHCHOH—CH₂—

It will be appreciated that the individual steroisomers of the compounds of the invention can readily be obtained by conventional methods. Thus, for example, the individual optically active isomers may be obtained by using optically active aminos to introduce the 2,3-dihydroxypropyl groups; thus in preparing the isomers of compound 1, the two 2,3-dihydroxypropyl groups are normally introduced simultaneously and use of the same optically active reagent avoids the production of meso isomers. Thus, the compound of formula II will for this purpose be a d,d- or an l,l- enantiomer. Separate optical isomers of the compounds of formula I can, if required, be mixed in equal proportions to produce a racemate. Such optically active isomeric material produced in this way is particularly water-soluble.

Alternatively, a mixture of isomers produced by using a racemic amine to introduce the 2,3-dihydroxypropyl groups may be subjected to fractionation. In particular, a concentrated solution of the mixed isomers of compound I formed by using racemic 2,3-dihydroxypropylamine in the foregoing synthesis, can be fractionally crystallised to yield a crystalline meso isomer and a mother liquor containing soluble isomeric material which can then, if desired be isolated by concentration and evaporation or the mother liquor may be used directly as a radiopaque.

Where it is desired to prepare optically active or racemic compounds of the invention from optically active or racemic starting materials compounds of formula I (wherein R represents the group —CH₂CH₂OH) in optically active or racemic form may be prepared by reacting a compound of formula II in optically active or racemic form with an appropriate hydroxyethylating agent.

Similarly compounds of formula I (wherein R represents the group —CH₂CHOHCH₂OH) in optically active or racemic form may be prepared by reacting a compound of formula II in optically active or racemic form with an appropriate hydroxypropylating agent in optically active or racemic form.

The following Examples are given by way of illustration only:

Preparation of Starting Materials (A)

5-Nitro-N,N'-bis(2,3-dihydroxypropyl)-isophthalamide (a) Dimethyl 5-nitroisophthalate (215 g) and 1-amino-2,3-propandiol (196 g) were refluxed in methanol (500 ml). After twenty hours the solution was cooled and stored in a refrigerator overnight. The product was then collected on a filter and washed with methanol. Yield: 270 g (84%). Melting point: A sample sintered at about 114° C. and melted at 128°–132° C.

(Found: C, 46.90; H, 5.11; N, 11.41. Calc. for $C_{14}H_{19}N_3O_8$: C, 47.06; H, 5.36; N, 11.76).

(b) (+)-5-Nitro-N,N'-bis(2,3-dihydroxypropyl)-isophthalamide

The (+)-amide was prepared from dimethyl 5-nitroisophthalate (13.6 g) and (+)-3-aminopropanediol-1,2 (11.95 g) in a similar manner to that described in (a) above. Yield: 15.0 g (74%). $[\alpha]_{546} = +31.5°$; $[\alpha]_{578} = +27.8°$ (c=4.2, MeOH: H$_2$O=60:40).

The substance became an unclear melt at 130°-133°, when heated in a capillary tube.

Analysis—Found: C, 47.15; H, 5.22; N, 11.27. Calc. for C$_{14}$H$_{19}$N$_3$O$_8$: C, 47.06; H, 5.36; N, 11.76.

TLC was performed on precoated plates (Silica Gel 60 F-254, Merck AG) and developed in A. MeOH:CHCl$_3$ = 30:70 R$_f$=0.38.
B. n-BuOH:HOAc:H$_2$O = 50:11:25 R$_f$=0.49.

(c) (−)-5-Nitro-N,N'-bis(2,3-dihydroxypropyl)-isophthalamide

The (−)-amide was prepared from (−)-3-aminopropanediol-1,2 (7.85 g) and dimethyl 5-nitroisophthalate (9 g) in a similar manner to that described in (a) above. Yield: 9.3 g (69%) $[\alpha]_{546} = -31.0°$; $[\alpha]_{578} = -27.2°$ (c=3.1, MeOH:H$_2$O=60:40).

The substance became an unclear melt at 135°-137°, when heated in a capillary tube.

Analysis—Found: C, 46.91; H, 5.49; N, 11.72. Calc. for C$_{14}$H$_{19}$N$_3$O$_8$: C, 47.06; H, 5.36; N, 11.76.

TLC was performed as described in (b) above.
System A: R$_f$=0.38.
System B: R$_f$=0.49.

(B)
5-Amino-2,4,6-triiodo-N,N'-bis(2,3-dihydroxypropyl)-isophthalamide (a) 5-Nitro-N,N'-bis(2,3-dihydroxypropyl)-isophthalamide (18.1 g) was suspended in water (250 ml), conc. hydrochloric acid (4.2 ml) and 10% PdO/charcoal (0.5 g) were added, and the mixture hydrogenated in a Parr apparatus for one day. After filtration the filtrate was heated at 80°-90° C. and 3.88 M NaICl$_2$ (42.5 ml) was added through a dropping funnel over a period of about one hour. The solution was heated for a further two and a half hours. After cooling to room temperature the product crystallized out.

Yield: 25.1 g (71%). The product sintered at 177°-179° C. and was decomposed at 195° C. by heating in a capillary tube.

(Found: C, 23.86; H, 2.49; I, 53.7; N, 5.94. Calc. for C$_{14}$H$_{18}$I$_3$N$_3$O$_6$: C, 23.85; H, 2.57; I, 54.00; N, 5.96).

(b) (+)-5-Amino-2,4,6-triiodo-N,N'-bis(2,3-dihydroxypropyl)-isophthalamide

The compound was prepared from (+)-5-nitro-N,N'-(2,3-dihydroxypropyl)-isophthalamide (14.25 g) by reducing bis—the nitro group with hydrogen and palladium on charcoal and finally iodinating with an aqueous solution of NaICl$_2$ in a similar manner to that described in B (a) above. Yield: 22.3 g (79%). $[\alpha]_{546} = +3.7°$; $[\alpha]_{578} = +3.5°$ (c=4.4; DMF:H$_2$O=2:8).

The substance started melting at 204° and was decomposed at 213°.

Analysis—Found: C, 23.87; H, 2.60; I, 53.4; N, 6.01. Calc. for C$_{14}$H$_{18}$I$_3$N$_3$O$_6$: C, 23.85; H, 2.57; I, 54.00; N, 5.96.

TLC was performed as described in A(b) above.
R$_f$=0.38 n system A.
R$_f$=0.50 in system B.

(c) (−)-5-Amino-2,4,6-triiodo-N,N'-bis(2,3-dihydroxypropyl)-isophthalamide

The laevorotatory compound was prepared from (−)-5-nitro-N,N'-bis(2,3-dihydroxypropyl)-isophthalamide (6.2 g) in a similar manner to that described in B(a) above. Yield: 9.3 g (76%) $[\alpha]_{546}=3.8°$; $[\alpha]_{578}=-3.4°$ (c=4.4; DMF:H$_2$O=20:80). The substance started melting at 203° and decomposed at 217°.

Analysis—Found: C, 23.72; H, 2.62; I, 53.2; N, 5.81. Calc. for C$_{14}$H$_{18}$I$_3$N$_3$O$_6$: C, 23.85; H, 2.57; I, 54.00; N, 5.96.

TLC was performed as described in A(b) above.
R$_f$=0.38 in system A.
R$_f$=0.50 in system B.

(C)
5-Acetamido-2,4,6-triiodo-N,N'-bis(2,3-dihydroxypropyl)-isophthalamide (a) 5-Amino-2,4,6-triiodo-N,N'-bis(2,3-dihydroxypropyl)-isophthalamide (110 g) was suspended in acetic anhydride (480 ml) and heated to 50° C. Concentrated sulphuric acid (3 ml) was then added. The starting material was dissolved after a few minutes, and the reaction mixture was heated at 60° C. for 75 minutes. After cooling the solution was concentrated in vacuo and the residue dissolved in methanol (300 ml). After dilution with water (150 ml) the solution was heated to 50° C. and the pH adjusted to about 10.5 by adding 10 N sodium hydroxide. When the pH decreased, it was adjusted by adding more 10 N sodium hydroxide in such a manner that the pH was kept at 10.0-10.9. After 4-5 hours the pH didn't decrease, and the hydrolysis was complete. The reaction mixture was cooled to room temperature and neutralized by adding hydrochloric acid. After stirring overnight the product was collected on a filter and washed with water.

Yield: 94 g (80%). M.p.: 275° C. dec.

The IR spectrum was identical with the IR spectrum of a compound previously characterised as the title compound.

Found: I, 50.3. Calc. for C$_{16}$H$_{20}$I$_3$N$_3$O$_7$: I, 50.95).

(b) (+)-5-Acetamido-2,4,6-triiodo-N,N'-bis(2,3-dihydroxypropyl)-isophthalamide

The dextrorotatory compound was prepared from (+)-5-amino-2,4,6-triiodo-N,N'-bis(2,3-dihydroxypropyl)-isophthalamide (21 g) by acetylation and a subsequent hydrolysis at pH 10-11 in a similar manner to that described in C(a) above. Finally the product was recrystallized from water. Yield: 13.6 g (61%) $[\alpha]_{546} = +4.0°$; $[\alpha]_{578} = +3.8°$ (c=4.5; DMF:H$_2$O=2:8).

Melting Point: 285°-289° dec.

Analysis—Found: C, 25.80; H, 2.50; I, 50.6; N, 5.71. Calc. for C$_{16}$H$_{20}$I$_3$N$_3$O$_7$: C, 25.72; H, 2.70; I, 50.95; N, 5.62.

TLC was performed as described in A(b) above.
R$_f$=0.30 in system A.
R$_f$=0.39 in system B.

(c) (−)-5-Acetamido-2,4,6-triiodo-N,N'-bis(2,3-dihydroxypropyl)-isophthalamide

The (−)-compound was prepared from (−)-5-amino-2,4,6-triiodo-N,N'-bis(2,3-dihydroxypropyl)-isophthalamide (14 g) in a similar manner to that described in C(a) above. The product was purified by recrystallisation from water.

Yield: 9 g (61%) $[\alpha]_{546}=-4.2°$; $[\alpha]_{578}=-3.8°$ (c=4.5; DMF:H$_2$O=2:8).

Melting point: 287°-289° dec.

Analysis—Found: C, 25.77; H, 2.72; I, 50.7; N, 5.62. Calc. for $C_{16}H_{20}I_3N_3O_7$: C, 25.72; H, 2.70; I, 50.95; N, 5.62.

TLC was performed as described in A(b) above.

$R_f=0.30$ in system A.

$R_f=0.39$ in system B.

EXAMPLE 1

5-(N-2-Hydroxyethylacetamido)-2,4,6-triiodo-N,N'-bis(2,3-dihydroxypropyl)isophthalamide (a) 5-Acetamido-2,4,6-triiodo-N,N'-bis(2,3-dihydroxypropyl)-isophthalamide (22.4 g, 30 mmole) was dissolved in a mixture of propylene glycol (65 ml) and 5.0 N sodium methoxide (9.6 ml; 48 mmole) by heating. The excess of methanol was evaporated in vacuo. The solution was then heated on an oil bath at 50° C. and 2-chloroethanol (3 ml, 45 mmole) was added under vigorous stirring. After five hours the reaction mixture was cooled to room temperature and the reaction product precipitated by adding the reaction mixture, through a dropping funnel, to acetone (1 l) with stirring. The mixture was stored at −20° C. overnight, filtered off, suspended in acetone twice and dried. Yield: 24.8 g. The product was then dissolved in water (100 ml) and the solution extracted with phenol (3×20 ml+2×10 ml). The combined phenol extracts were washed with water (2×20 ml) diluted with ether (160 ml) and extracted with water (4×30 ml). Finally, the aqueous layer was washed with ether (4×30 ml). The aqueous solution was evaporated to dryness in vacuo. The product was then dissolved in 80% (v/v) aqueous methanol (100 ml) and stirred with Dowex anion exchange resin 1×4 (3 g) and Amberlite cation exchange resin 1R 120 H (1.5 g) for four hours. After filtration the filtrate was evaporated to dryness in vacuo. Yield: 19 g (80%). The substance was dissolved with stirring in n-butanol (315 ml) by heating in an oil bath at 90° C. After seeding, crystals insoluble in hot n-butanol started crystallizing after half an hour. After heating for two days the mixture was filtered while hot. The product was dissolved in water, and the solution evaporated to dryness in vacuo. Yield: 14 g. The recrystallization procedure from n-butanol was repeated. Finally, the product was dissolved in water, heated with charcoal and evaporated in vacuo to dryness. Yield: 9.9 g. Melting point: 180°-220° C. dec. (Found: C, 26.88; H, 3.05; I, 48.12; N, 5.01. Calc. for $C_{18}H_{24}I_3N_3O_8$: C, 27.33; H, 3.06; I, 48.12; N, 5.31).

(b) Separation of the soluble and insoluble components of 5-(N-2-hydroxyethylacetamido)-2,4,6-triiodo-1,3-bis-N,N'-(2,3-dihydroxypropyl) isophthalamide The amorphous material is dissolved with stirring in two to five times its own weight of cold distilled water. When dissolution is complete, the stirring is stopped and the solution is kept at room temperature protected from sunlight and other strong light for a period of one to five weeks. The suspension may be stirred occasionally. The process of crystallisation may be followed by measuring the refractive index of the supernatant; when this is constant the insoluble material is collected by filtration. The soluble part is obtained by evaporation under reduced pressure at a temperature between 20° and 80°. Approximately equal amounts of soluble and insoluble component are obtained. The composition of each component, as concerns the amount of the other component still present, can be determined by nuclear magnetic resonance spectroscopy. A proton nmr spectrum of a 10% w/v solution of the compound in deuteropyridine is recorded on a very high field nmr instrument, operating at a frequency of 250 MHz or above. On expanding the spectrum to a scale of 5 Hz or less per centimeter, the acetyl methyl group of the exo N-hydroxyethyl acetamido group is found at about 1.4–1.5 ppm from TMS (variation due to temperature and concentration) and two sharp singlets separated by about 0.01 ppm (2.3 Hz at 250 MHz, 2.6 Hz at 270 MHz). The peak at slightly lower field is from the soluble component, that at higher field is from the insoluble component, and the relative intensities of these peaks allow the composition of any product to be determined.

(c) (−)-5-(N-2-Hydroxyethylacetamido)-2,4,6-triiodo-N,N'-bis(2,3-dihydroxypropyl)-isophthalamide The laevorotatory compound was prepared from (−)-5-acetamido-2,4,6-triiodo-N,N'-bis(2,3-dihydroxypropyl)-isophthalamide (8 g) in a similar manner to that described in Example 1(a). After the reaction was completed, the reaction mixture was diluted with water, neutralized with hydrochloric acid and evaporated in vacuo. The oily residue was dissolved in methanol (50 ml) and the salts filtered off (filtrate F). 10–15 ml of Silica gel (0.063–0.200 mm) was added to 25 ml of the filtrate F and the slurry evaporated to dryness in vacuo. A slurry of this in a mixture of $MeOH/CHCl_3$ (20:80) was applied to a silica gel (particle size 0.063–0.200 mm) column (35×2.5 cm) for chromatography. The elution started with a mixture of $MeOH/CHCl_3$ (20:80) and was gradually changed to a mixture of $MeOH/CHCl_3$ (60:40). The column chromatography was followed by TLC (system A). The fractions containing the pure product were collected and evaporated in vacuo. The residue was dissolved in water and treated with charcoal at room temperature. After filtration, the filtrate was evaporated to dryness in vacuo. Then the product was dissolved in 80% (v/v) aqueous methanol (20 ml) and stirred with Amberlite cation exchange resin IR 120 H and Dowex anion exchange resin 1×4 in sufficient amounts to remove the salts. After filtration, the solution was evaporated to dryness in vacuo, the residue dissolved in water and evaporated to dryness again.

The remainder of the methanolic filtrate F was treated in the same manner. Yield: 4.4 g (52%). $[\alpha]_{546}=-5.5°$; $[\alpha]_{578}=-4.7°$ (c=20.0, water).

The melting point of the substance is not very characteristic. When heated in a capillary tube, the solid became an unclear melt at about 180° which liberated iodine by further heating. TLC was performed as described in A(b) above.

$R_f=0.31$ in system A 0.31 (endo-isomer) and $R_f=0.42$ (exo-isomer) in system B.

Analysis—Found: C, 27.58; H, 3.10; I, 48.2; N, 4.78. Calc. for $C_{18}H_{24}I_3N_3O_8$: C, 27.33; H, 3.06; I, 48.12; N, 5.31.

(d) (+)-5-(N-2-Hydroxyethylacetamido)-2,4,6-triiodo-N,N'-bis(2,3-dihydroxypropyl)-isophthalamide The dextrorotatory compound was prepared from (+)-5-acetamido-2,4,6-triiodo-N,N'-bis(2,3-dihydroxypropyl)-isophthalamide (8 g) in a similar manner to that described for the preparation of the corresponding laevorotatory compound (Example 1c). Yield: 3.8 g (45%) $[\alpha]_{546}=+5.5°$; $[\alpha]_{578}=+4.8°$ (c=20.0, water).

The melting point of the substance is not very characteristic. When heated in a capillary tube, the solid sintered at about 165° and liberated iodine at 205° by further heating. TLC was performed as described in A(b) above.

$R_f=0.31$ in system A 0.31 (endo-isomer) and $R_f=0.42$ (exo-isomer) in system B.

Analysis—Found: C, 27.56; H, 3.08; I, 48.0; N, 5.20. Calc. for $C_{18}H_{24}I_3N_3O_8$: C, 27.33; H, 3.06; I, 48.12; N, 5.31.

Aqueous solution of racemic 5-(N-2-hydroxyethylacetamido)-2,4,6-triiodo-N,N'-bis(2,3-dihydroxypropyl)-isophthalamide 624 mg of each of the enantiomers were mixed and dissolved in distilled water ad 2 ml, giving a clear solution which contained about 300 mg I/ml.

EXAMPLE 2

5-(N-2,3-Dihydroxypropylacetamido)-2,4,6-triiodo-N,N'-bis(2,3-dihydroxypropyl)isophthalamide 5-Acetamido-2,4,6-triiodo-N,N'-bis(2,3-dihydroxypropyl)isophthalamide (37.4 g; 50 mmole) was dissolved in propylene glycol (110 ml) by adding 5.3 M sodium methoxide (14.2 ml; 75 mmole) and heating in an oil bath at 50° C. When all or nearly all of the starting material was dissolved, the excess of methanol was evaporated in vacuo. After cooling to room temperature 3-chloropropane-1,2-diol (6.3 ml; 75 mmole) was added. When the reaction mixture was applied to TLC in system (B) after stirring for two days, two new spots with $R_f$ values 0.26 and 0.33 in a ratio of about 1:9 and less than 0.5% of the starting material with $R_f$ 0.42 were observed. The new spots were assumed to represent endo/exo isomers. The reaction mixture was evaporated in vacuo and the residue dissolved in methanol (125 ml). A small amount of undissolved material was filtered off and water (30 ml) added. This solution was treated with a mixture of Amberlite cation exchange resin IR 120H (27.5 g) and Dowex anion exchange resin 1×4 (50 g) for two hours. After filtration, the pH of the solution was adjusted to 4.9, and then evaporated in vacuo. The oily residue was triturated in butanol (125 ml). The product crystallized out following this treatment. After storing at −20° C., the product was filtered off. Then the product was dissolved in water, and the solution evaporated in vacuo. Yield 38 g.

Further, the product was dissolved in butanol (760 ml) at 90° C. and stirred at this temperature. Crystals insoluble in hot butanol started crystallizing after about one hour. The next day the hot mixture was filtered. The product was dissolved in water and the solution evaporated in vacuo. Yield: 27.6 g. This recrystallization procedure from butanol was repeated once. Finally, the product was dissolved in water and evaporated to dryness. The residue was redissolved in water and the solution evaporated in vacuo. Yield: 22 g. Melting point: 174°-180° C. (Found: C, 27.98; H, 3.38; I, 46.0; N, 5.24; O, 17.27. Calc. for $C_{19}H_{26}I_3N_3O_9$: C, 27.79; H, 3.19; I, 46.36; N, 5.12; O, 17.54).

EXAMPLE 3

Compound I for infusion, 150 mg I/ml

| Composition: | 1 liter |
| --- | --- |
| Compound I: | 312 g |
| Sodium calcium edetate: (ethylenediaminetetraacetate) | 0.2 g |
| Water for injection | ad 1000 ml |
| HCl 0.1M q.s. to make pH 5 | |

Manufacturing procedure:

Compound I and the edetate are dissolved in water for injection, ca. 950 ml. pH is adjusted to 5.0 by means of hydrochloric acid 0.1 M.

Water for injection is added to make 1000 ml.

The solution is membrane filtered and dispensed into bottles of 250 ml.

The bottles are autoclaved for 20 min. at 120° C.

EXAMPLE 4

Compound I for injection, 280 mg I/ml

| Composition: | 1 liter |
| --- | --- |
| Compound I: | 582 g |
| Sodium calcium edetate: | 0.2 g |
| Water for injection | ad 1000 ml |
| HCl 0.1M q.s. to make pH 5.0 | |

Manufacturing procedure: As Example 3.

The solution is dispensed into vials of 100 ml or ampoules of 20 ml.

EXAMPLE 5

Compound I for injection, 440 mg I/ml

| Composition: | 1 liter |
| --- | --- |
| Compound I: | 915 g |
| Sodium calcium edetate: | 0.25 g |
| Water for injection | ad 1000 ml |
| Hcl 0.1M q.s. to make pH 5.0 | |

Manufacturing procedure: As Example 3. The solution is dispensed into vials of 50 ml or ampoules of 20 ml. If a pH of 7.0-7.5 should be desired a physiological sterile buffer solution could be added immediately before injection.

EXAMPLE 6

Compound II for infusion, 150 mg I/ml

| Composition: | 1 liter |
| --- | --- |
| Compound II: | 324 g |
| Sodium calcium edetate: (ethylenediaminetetraacetate) | 0.2 g |
| Water for injection | ad 1000 ml |
| HCl 0.1M q.s. to make pH 5 | |

Manufacturing procedure:

Compound II and the edetate are dissolved in water for injection, ca. 950 ml. pH is adjusted to 5.0 by means of hydrochloric acid 0.1 M.

Water for injection is added to make 1000 ml.

The solution is membrane filtered and dispensed into bottles of 250 ml.

The bottles are autoclaved for 20 min. at 120° C.

We claim:

1. Compounds of the general formula:

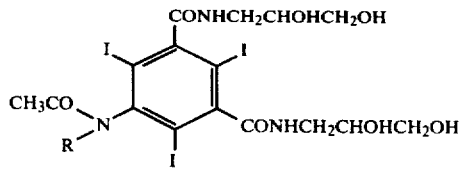

(wherein R represents the group —CH$_2$CH$_2$OH or —CH$_2$CHOHCH$_2$OH).

2. 5-(N-2-Hydroxyethylacetamido)-2,4,6-triiodo-N,N'-bis-(2,3-dihydroxypropyl)isophthalamide.

3. 5-(N-2,3-Dihydroxypropyl)-2,4,6-triiodo-N,N'-bis-(2,3-dihydroxypropyl)isophthalamide.

4. The compound:
(+)-5-(N-2-Hydroxyethylacetamido)-2-4,6-triiodo-N,N'-bis(2,3-dihydroxypropyl)isophthalamide;
(−)-5-(N-2-Hydroxyethylacetamido)-2,4,6-triiodo-N,N'-bis(2,3-dihydroxypropyl)isophthalamide; or
racemic 5-(N-2-Hydroxyethylacetamido)-2,4,6-triiodo-N,N'-bis(2,3-dihydroxypropyl)isophthalamide.

* * * * *